US007625340B2

(12) United States Patent
Särkelä

(10) Patent No.: US 7,625,340 B2
(45) Date of Patent: Dec. 1, 2009

(54) IDENTIFICATION OF A DOMINANT SIGNAL COMPONENT IN A BIOSIGNAL

(75) Inventor: Mika Särkelä, Helsinki (FI)

(73) Assignee: Instrumentarium Corporation, Helsinki (FI)

( * ) Notice: Subject to any disclaimer, the term of this patent is extended or adjusted under 35 U.S.C. 154(b) by 1153 days.

(21) Appl. No.: 11/002,402

(22) Filed: Dec. 2, 2004

(65) Prior Publication Data

US 2006/0135880 A1 Jun. 22, 2006

(51) Int. Cl.
  *A61B 5/00* (2006.01)
(52) U.S. Cl. .................... 600/300; 600/544; 600/546
(58) Field of Classification Search .................... None
  See application file for complete search history.

(56) References Cited

U.S. PATENT DOCUMENTS

| 6,032,072 | A | 2/2000 | Greenwald |
| 6,338,713 | B1 | 1/2002 | Chamoun et al. |
| 7,130,673 | B2 | 10/2006 | Tolvanen-Laakso et al. |
| 2004/0204656 | A1 | 10/2004 | Tolvanen-Laakso et al. |

FOREIGN PATENT DOCUMENTS

EP  1 468 646  10/2004

OTHER PUBLICATIONS

European Search Report dated Apr. 11, 2006.
H. Viertiö-Oja et al., "Description of the Entropy algorithm as applied in the Datex-Ohmeda S/5 Entropy Module", ACTA Anaesthesiol. Scand., vol. 48, Jan. 22, 2004, pp. 154-161.
R. E. Anderson, et al., "Entropy during propofol hypnosis, including an episode of wakefulness", Anaesthesia, vol. 52, Jan. 2004, pp. 52-56.
Hairong Zheng et al., "Advantages in using multi-frequency driving to enhance ultrasound contrast microbubble non-linearities for optimizing echo particle image velocimetry techniques", Biomedical Imaging: Macro to Nano, 2004. IEEE International Symposium on Arlington, VA Apr. 15-18, 2004, Piscataway, NJ, Apr. 15, 2004, pp. 500-503.
Roberto Massetani et al., "Alteration of Cardiac Function in Patients with Temporal Lobe Epilepsy: Different Roles of EEG-ECG Monitoring and Spectral Analysis of RR Variability", Epilepsia, No. 38, Mar. 1997, pp. 363-369.
Hans-Bernd Hopf et al., "Low-frequency Spectral Power of Heart Rate Variability is not a Specific Marker of Cardiac Sympathetic Modulation", Anesthesiology, vol. 82, No. 3, Mar. 1995, p. 619.

*Primary Examiner*—Robert L Nasser
(74) *Attorney, Agent, or Firm*—Andrus, Sceales, Starke & Sawall, LLP

(57) ABSTRACT

The invention seeks to provide a method and a system for identifying a dominant signal component in a biosignal including at least two signal components. A biosignal including a first signal component having a first frequency range and a second signal component having a second frequency range is obtained from a subject. First and second indicators are then determined, which characterize the probability distribution of a predefined property, such as frequency, of the biosignal on predetermined primary and auxiliary frequency bands, respectively. Based on the first and second indicators, the system detects which one of the first and second signal components is currently a dominant signal component in the biosignal. The knowledge of the dominant component may be utilized in different ways in different systems monitoring the state of the subject.

45 Claims, 9 Drawing Sheets

IDENTIFICATION OF A DOMINANT SIGNAL COMPONENT IN A BIOSIGNAL

FIELD OF THE INVENTION

The present invention relates generally to the identification of a dominant signal component in a biosignal measured from a subject. The invention is primarily intended for identifying the presence of ocular activity in an electroencephalogram (EEG) or in a magnetoencephalogram (MEG) signal, although it may also be used in connection with any other biosignal measurements in which the presence of certain signal components of interest may be detected with the same mechanism.

BACKGROUND OF THE INVENTION

A bioelectric or biomagnetic signal measured from the forehead of a subject includes different signal components, originating from physiological activities of brain, eyeballs and facial muscles, for example. The study of electromagnetic activity generated by brain has a significant role in physiological and clinical settings. The electrical component of the brain activity is called the electroencephalogram (EEG) and its magnetic counterpart the magnetoencephalogram (MEG). The EEG and the MEG have different sensitivities to sources of different orientations and locations but the primary currents causing the said signals are the same. Similarities between these waveforms are therefore to be expected.

Analogically, the electrical activity of muscles is called the electromyogram (EMG) and the ocular activity the electrooculogram (EOG). The EMG and the EOG have their magnetic counterparts as well. However, they are not in practical use at the moment and are mainly considered as artifacts.

Ocular electromagnetic activity is mainly within a frequency range of 0 to 8 Hz, whereas the electromagnetic activity of the facial muscles is mainly at frequencies above 20 Hz. In this context, ocular activity refers to eye movements or eye blinks. Eye movements are movements of the eyeball. The eyeball may be modelled as an electrical dipole, because the retina is positively and the cornea negatively charged. Eye movements produce large electromagnetic fields measurable on the forehead, which attenuate proportionally to the square of the distance from the eyes. An eye blink, i.e. the temporary closure of the eyelid, generates an electromagnetic field due to the motion of the eyelid over the cornea. In electrical engineering terms, an eye blink thus means a short circuit caused by the closure of the eyelid.

Low-frequency brain activity lies within the same frequency band as the ocular activity. Below, ocular activity and low-frequency brain activitivity are discussed briefly.

The EOG is a time-varying signal, which includes asymmetrical wave forms in time-domain. Successive EOG waves do not follow each other immediately. In practice, this means that in a given time window the signal includes both periods containing EOG activity and periods not containing EOG activity. Therefore, the statistical properties of an EOG signal change in a given time window, and the signal can be said to be non-stationary. A further characteristic feature of the EOG is that periods between successive EOG waves are unpredictable. Therefore, the EOG may also be said to be non-periodical. Traditional use of the EOG is in sleep recordings.

Low-frequency brain activity refers to Delta and Theta rhythms. The Delta rhythms are commonly defined as the activity between 1 and 4 Hz. The Delta rhythms have two distinct origins: one is in the cortex and the other in the thalamus. The Theta rhythms are usually considered as the activity within the frequency range of 4 to 7 Hz. Both the Delta and Theta rhythms are rare in a healthy, awake adult. However, they arise during sleep or drug-induced anesthesia or sedation.

Low-frequency brain activity is periodical in nature. A single wave of low-frequency brain activity of a healthy person is symmetrical in time-domain. Additionally, brain activity is stationary, since successive brain waves typically follow each other immediately. The above-mentioned features lead to the fact that the brain activity of a sleeping or anesthetized person includes distinct peaks below 10 Hz, called the dominant frequencies.

The above-described signals may be used in various ways to assess the state of a subject. This is discussed briefly in the following.

The EEG is a well-established method for assessing brain activity by recording and analyzing the weak biopotential signals generated in the cortex of the brain with electrodes attached on the skin of the skull. The EEG has been in wide use for decades in basic research of the neural systems of the brain, as well as in clinical diagnosis of various neurophysiological diseases and disorders. During the past few years, several commercial devices for measuring the level of consciousness and/or awareness in a clinical set-up during anesthesia have become available. These devices, which have been introduced by Aspect Medical Systems (Bispectral Index) and Datex-Ohmeda (Entropy™), for example, describe EEG characteristics as a single number indicative of the said level.

A signal from an awake or lightly sedated subject includes eye movements and blinks, which disappear before the surgical level of anesthesia is reached. The EEG activity of a healthy awake patient concentrates mainly on higher frequencies, whereas in deepening anesthesia the activity becomes slower and low-frequency EEG starts to dominate. Correct classification of the ocular and low-frequency EEG activities becomes therefore an important issue for the recognition of a wake state and the states of anesthesia or sedation. This is especially important at the conduction of anesthesia, where the transition from a conscious to an unconscious state takes place quickly. The patient often moves his/her eyes even just before unconsciousness is reached. This is illustrated in FIG. 1, which shows an EEG signal measured when the patient is about to reach an unconscious state. The peaks denoted with reference number 10 originate from eye movements. These peaks disappear when unconsciousness is reached.

It is thus difficult to track the change of the state of the patient. However, if the change cannot be detected quickly, the exact time of reaching unconsciousness is impossible to determine.

For these purposes, a technique based on the concept of near-field or far-field potentials may be used, as described in the U.S. Pat. No. 6,032,072. In practice, this technique requires at least two channels to be measured, the first channel representing the near-field potential and the second channel the far-field potential.

The above-described signals may also be used in sleep studies. Polygraphic recording of sleep typically includes monitoring of EEG, ECG (electrocardiogram), EOG, EMG, and respiration signals. At least a single channel EEG and a single channel EOG measurement is then required. The EOG electrodes are connected to the corners of both eyes, vertically at different levels. Based on the EEG and EOG characteristics, sleep is normally categorized into six different levels: awake, S1, S2, S3, S4, and REM (Rapid Eye Movement). Eye movements are most prominent at the awake and REM levels. REM periods are identified based on the existence of saccadic eye movements. Low-frequency EEG appears commonly at the levels S2, S3 and S4. For the correct classification, it is important to distinguish EOG from frontal Delta activity. Traditionally, piezoelectric sensors are connected to the eyelid to identify the eye movements.

A further application of the above-mentioned signals is the monitoring of the state of alertness, which has a number of clinical applications. By means of these systems, shift workers, truck drivers, train operators, and other individuals who work during hours of maximum sleepiness may be notified when they become too drowsy. Both EEG and EOG analysis may be used for defining the level of alertness. In an alert subject, the eye movements are fast, whereas in a lowered state of alertness the eye movements become slower. Fatigue, drugs and alcohol, for example, slow down saccadic eye movements. There is a growing evidence indicating that sleep loss and associated decrements in neurobehavioral function are reflected in the spectral composition of the EEG during wakefulness as well as in the incidence of slow eye movements recorded by the EOG. The incidence of slow eye movements during wakefulness increases during periods of sleep loss and correlates with changes in alertness and psychomotor vigilance.

Spectral entropy derived from the frequency range of the EOG may be utilized for monitoring alertness. The spectrum of saccadic eye movements lies principally at higher frequencies than the spectrum of slow eye movements. Additionally, the wave form of saccadic eye movements includes more rapid changes than that of slow eye movements, being therefore less similar to sine wave than the waveform of slow eye movements. As a result, the spectral entropy of saccadic eye movements is higher than that of slow eye movements.

As discussed above, correct identification of ocular and low-frequency brain activity is important in many monitoring or control systems, such as in sleep diagnosis and in assessment of the depth of anesthesia or sedation. However, these two activities cannot be identified based on the spectral power since the frequency bands of the said two activities are overlapping and since the spectral powers of biosignals are known to be subjective. To illustrate the problem, FIG. 2 shows an example of the spectra of two signals. In the figure, the continuous line represents the power spectrum of a signal including EEG, EOG, and EMG components, while the dashed line represents the power spectrum of a pure EEG signal. As can be seen, the spectra are very much alike at low frequencies.

The correct identification of the said two activities is therefore complicated. As discussed above, the identification normally requires at least two measurements signals, one for each signal component of interest, coupled with complicated signal processing.

The present invention seeks to alleviate the above problems related to the detection and separation of the EEG and EOG signals and to bring about a method by means of which the fidelity of the EEG and/or the EOG signals may be improved in an uncomplicated way using only a single measurement signal obtained from the subject.

SUMMARY OF THE INVENTION

The present invention seeks to provide a method and a system for identifying a dominant signal component in a biosignal including at least two signal components. In this context, the signal components refer to different signals that mingle at the measuring electrodes and thus appear in a biosignal measured through the said electrodes. Due to this, the measured biosignal is also termed the composite signal in the following description.

The solution of the invention is primarily intended for identifying whether ocular activity or low-frequency brain activity is dominant in a biosignal measured from a subject, although the solution may be used in connection with other biosignal measurements in which the presence and/or absence of certain signal components of interest may be detected with the same mechanism. The invention further seeks to provide an uncomplicated method and system, which do not require a multi-channel signal to be obtained from the subject.

The invention rests on characteristic differences of the signal components of interest, which translate to different probability distributions. These differences can therefore be seen in indicators indicating how a predefined property of the signal is distributed over appropriately selected frequency bands, which the signal components occupy differently. An estimate of the proportions of the signal components of interest may therefore be obtained, i.e. the dominant one of the signal components of interest may be identified, when such indicators are compared with each other or when a new indicator is calculated based on the indicators and the new indicator is compared with a predefined threshold. The probability distribution may be calculated in respect of frequency, for example, in which case indicators indicative of spectral entropy may be used, since spectral entropy describes how flat the spectral distribution is, i.e. how heavily the signal power is concentrated around certain distinct frequencies. However, as discussed below, the probability distribution may also be calculated in respect of amplitude.

Thus one aspect of the invention is providing a method for identifying a dominant signal component in a biosignal obtained from a subject. The method includes the steps of obtaining a biosignal from a subject, the biosignal including a first signal component having a first frequency range and a second signal component having a second frequency range and determining a first indicator characterizing the probability distribution of a predefined property of the biosignal on a primary frequency band including at least part of the first frequency range. The method further includes determining a second indicator characterizing the probability distribution of said predefined property of the biosignal on an auxiliary frequency band including at least part of the second frequency range and identifying, based on the first and second indicators, which one of the first and second signal components is currently a dominant signal component in the biosignal.

Another aspect of the invention is that of providing a system for identifying a dominant signal component in a biosignal obtained from a subject. The system includes measurement means for obtaining a biosignal from a subject, the biosignal including a first signal component having a first frequency range and a second signal component having a second frequency range. The system also includes first calculation means for determining a first indicator characterizing the probability distribution of a predefined property of the biosignal on a primary frequency band including at least part of the first frequency range and second calculation means for determining a second indicator indicative of the probability distribution of the predefined property of the biosignal on an auxiliary frequency band including at least part of the of the second frequency range. The system further includes identification means for identifying, which one of the first and second signal components is currently a dominant signal component in the biosignal, the identification means being responsive to the first and second calculation means.

In one embodiment, the invention provides a computer program product for identifying a dominant signal component in a biosignal obtained from a subject. The computer program product includes a first program code portion configured to determine a first indicator characterizing the probability distribution of a predefined property of the biosignal on a selected primary frequency band, a second program code portion configured to determine a second indicator characterizing the probability distribution of the predefined property of the biosignal on a selected auxiliary frequency band, and a third program code portion configured to identify, based on the first and second indicators, which one of the first and second signal components is currently a dominant signal component in the biosignal.

By means of the solution of the invention, the quality of a biosignal comprising several mingled signal components may be improved in an uncomplicated manner. This is due to the fact that the invention allows the use of only one measurement channel coupled with standard and robust signal processing techniques. Furthermore, the mechanism is fast, which is important as a change in the state of the subject may occur quickly.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 3 to 12 in the appended drawings, wherein.

DETAILED DESCRIPTION OF THE INVENTION

Figure 1:
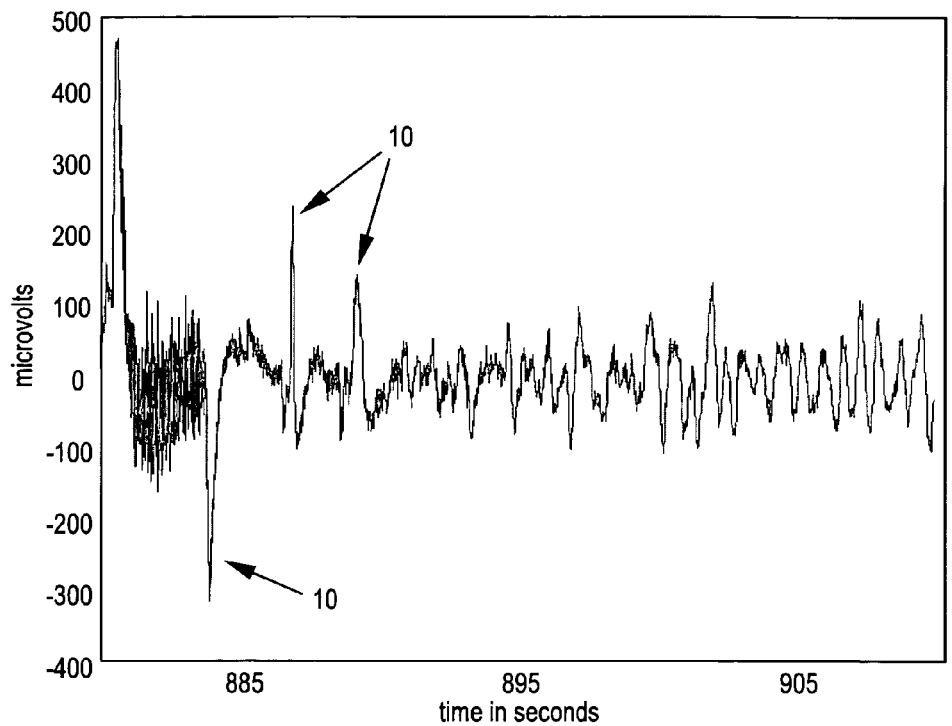
FIG. 1 shows an example of an EEG signal comprising several signal components.

In the present invention, a single-channel biosignal is measured from the subject in a known manner. Since several biopotentials normally mingle at the measuring electrodes, the biosignal, which is also termed the composite signal, may include several signal components, such as EEG, EOG, and EMG components.

The mechanism of the invention identifies the relationship between two signal components of interest, which share the same frequency range, and which are therefore difficult to uncouple by a filter. Below, the signal components of interest are termed the first and the second signal components. At one time instance, one of these signal components is dominant over the other and the dominant component is identified. It is further assumed below that the identification is based on indicators indicative of spectral entropies on predefined, component-specific frequency bands. These frequency bands are determined prior to the actual measurement. This is discussed below.

Unless the said two signal components share the common frequency range, it is defined that the signal component with a wider frequency range is the first signal component. The invention thus utilizes a priori information of the composite signal for the definition of optimal frequency bands. In one embodiment of the invention, the frequency bands from which the spectral entropies are calculated may be selected using the following rules:

1) A frequency band is first determined, which maximally covers the frequency range of the first signal component and which is at the same time minimally disturbed by any undesired signal component within the composite signal. Below, this frequency band is called the primary frequency band.

2) A second frequency band is then determined, which maximally covers the frequency range of the second signal component and which is at the same time minimally disturbed by any undesired signal component within the composite signal. Below, this frequency band is termed the auxiliary frequency band.

In the above rules, the term "any undesired signal component" refers to any other signal component which the composite signal may include in addition to the first and second components, which are the components of interest. Thus, in this embodiment, the first and second signal components do not belong to the group of "undesired signal components". There are thus two signal components of interest, i.e. the first and second signal component, and the remaining components of the composite signal belong to the group of "undesired signal components". It is also to be noted that the above rules give the guidelines according to which the primary and auxiliary frequency bands may be selected. However, the exact limits of the said bands may still vary to a certain extent even in a single application, since minor changes in the said values do not substantially affect the performance of the method and since the "undesired signal components" do not normally have any exact frequency limits.

Figure 3:
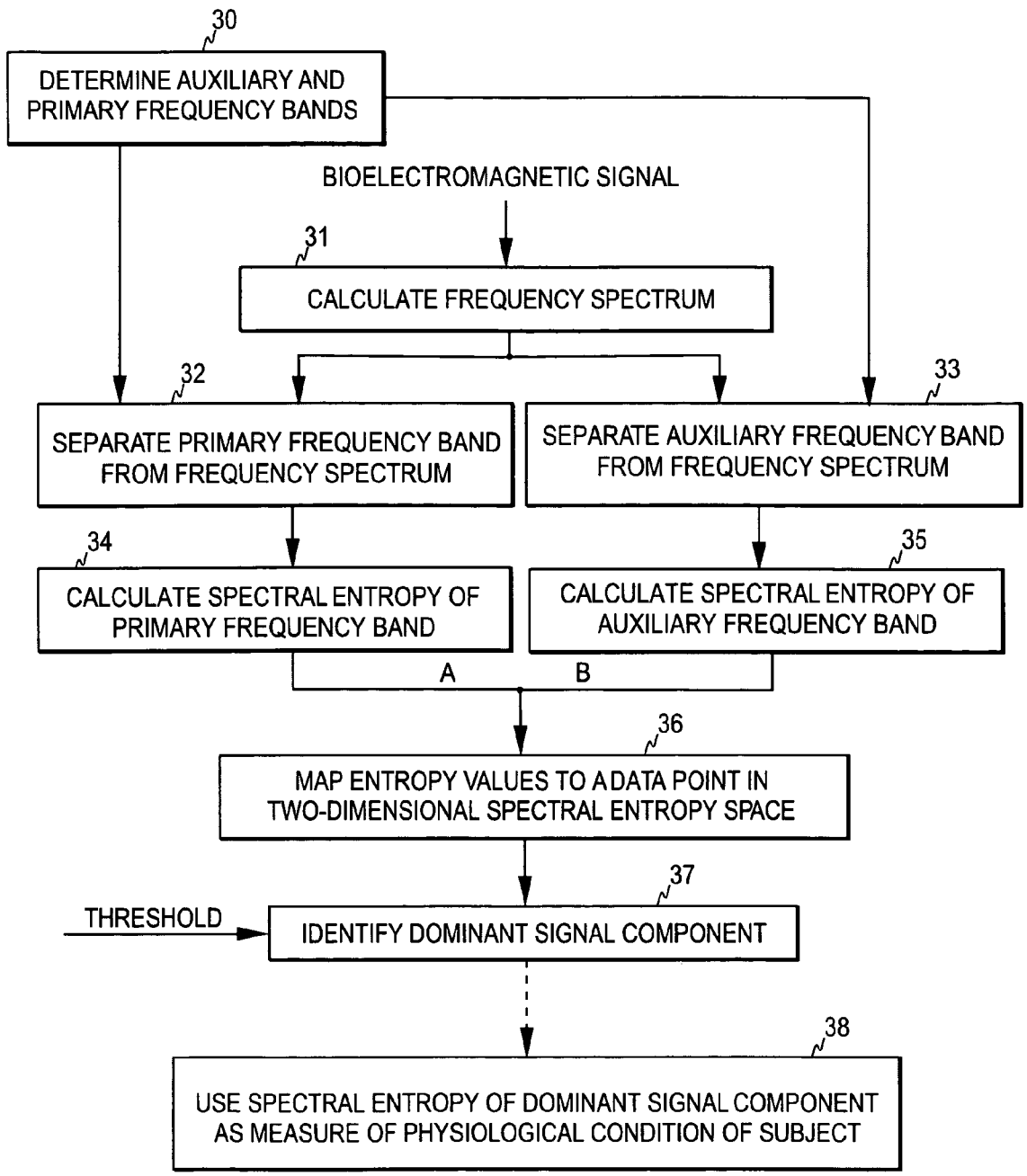
FIG. 3 is a flow diagram of one embodiment of the invention, in which the decision-making is based on a two-dimensional indicator space.

Below, the invention will be described assuming that the first and second signal components are the EEG and the EOG components, respectively. FIG. 3 illustrates one embodiment of the invention suitable for identifying which one of the said components is the current dominant component in the measured composite signal, which is thus an EEG signal comprising an EOG signal, and possibly also other components, such as an EMG component.

Since the total frequency range of an EEG signal is wider than that of an EOG signal, the EEG component is the above-mentioned first component and the EOG component is the above-mentioned second component. The frequency range of an EEG signal may extend as high as 80 Hz. However, as an EMG component begins to disturb the EEG spectrum at frequencies above about 20 Hz and as in the frequency range of 0 to 1 Hz the spectrum may be disturbed by an artifact originating from the movement of the patient, a frequency range of 1 to 19 Hz may be selected as the primary frequency band. The frequency range of the EOG component is typically from 0 to 8 Hz. A frequency range of 1 to 8 Hz may thus be selected as the auxiliary frequency range, since it is minimally affected by the undesired signal components within the composite signal. The primary and auxiliary frequency bands are determined at step 30, which is performed prior to the actual measurement.

Single-channel signal data is then obtained from the subject. Single-channel signal data here refers to a single biosignal, which is in this case an EEG signal, measured from the subject. The signal data may be collected in a conventional manner by converting the analog signal received from the electrodes into digital format and storing the digital data for further processing. The processing of the digitized data typically uses sets of sequential signal samples representing finite blocks of time, commonly termed "epochs".

A spectrum analysis is then performed at step 31, in which a frequency spectrum is calculated for the composite signal obtained from the subject. Typically, a Fourier transform, such as the Discrete Fourier Transform (DFT), may be used to calculate the frequency spectrum. However, any other suitable method, such as a wavelet transform, may also be used to calculate the frequency spectrum.

As is commonly known, using the DFT the frequency domain representation X(f) of a signal x(nT), i.e. a signal sampled at time intervals T, is as follows:

$$X(f) = \sum_{n=0}^{N-1} x(nT) e^{-j2\pi f n/N} \quad (1)$$

The absolute value of X(f) is called an amplitude spectrum. A power spectrum P(f) is obtained by multiplying X(f) with its complex conjugate X^(f):

$$P(f) = X(f) * X^{\wedge}(f) \quad (2)$$

The power spectrum is then normalized so that its sum over the frequency range of interest $[f_1, f_2]$ is equal to one. This is conducted with the help of a normalization constant $C_n$.

$$\sum_{f_i=f_1}^{f_2} P_n(f_i) = C_n \sum_{f_i=f_1}^{f_2} P(f_i) = 1 \quad (3)$$

The spectral entropy over the frequency range of interest $[f_1, f_2]$ may then be calculated, for example, by means of equation (4) as follows:

$$S[f_1, f_2] = \sum_{f_i=f_1}^{f_2} P_n(f_i) \log \frac{1}{P_n(f_i)}. \quad (4)$$

After the frequency spectrum has been calculated, the primary and auxiliary frequency bands are separated from the calculated spectrum at steps 32 and 33, respectively, whereby the frequency spectrums of the said bands are obtained. At steps 32 and 33, the signal is thus subjected to a spectral decomposition, in which the values corresponding to the primary and auxiliary bands, respectively, are extracted from the values calculated at step 31.

A first indicator and a second indicator are then calculated at steps 34 and 35, respectively. The first indicator is indicative of the spectral entropy of the composite signal on the primary frequency band, while the second indicator is indicative of the spectral entropy of the composite signal on the auxiliary frequency band. The two entropy values obtained are denoted with A and B in the figure. A new entropy value pair (A, B) is obtained for each epoch. The rate at which a new value pair is calculated may vary. Typically, the length of one epoch is of the order of a few seconds, such as 5 seconds.

Figure 4:
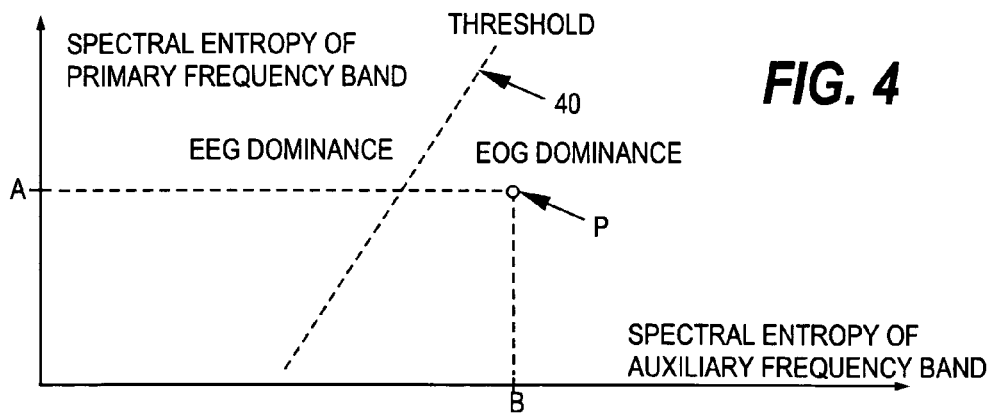
FIG. 4 illustrates one embodiment of the decision-making process of the invention.

The entropy value pair (A, B) calculated is then mapped at step 36 to a point in a two-dimensional spectral entropy space, where the spectral entropy of the primary frequency band represents the first dimension and the spectral entropy of the auxiliary frequency band the second dimension. The mapping process is illustrated in FIG. 4. As shown in the figure, for each entropy value pair (A, B) a data point P is obtained, whose abscissa is determined by one entropy value (here B) and whose ordinate by the other entropy value (here A) in the value pair.

With reference to FIG. 3 again, the dominant signal component is then identified at step 37, where the concept of linear classification may be applied. This involves using a pre-defined threshold line 40, shown in FIG. 4. The location of the data point in view of the threshold line determines, whether EEG or EOG dominance is involved, i.e. the threshold line is a line between the areas of "EEG dominance" and "EOG dominance". In this example, the line is defined by the equation y=kx+c, where x presents the entropy of the auxiliary frequency band, y the entropy of the primary frequency band, k is a slope, and c is a constant.

The threshold line may be defined based on entropy values measured from a (large) patient group and the system of the invention may make the decision on the dominant signal component after having defined on which side of the threshold line the data point defined by the entropy value pair is.

The decision on the dominant signal component may be made at each data point. The system may also make a final decision on the dominant component on a majority basis, for example, after having made a decision at a certain number of successive data points.

The decision may also be made after a certain number of data points, without making a decision at each data point. Based on the data points obtained, various parameters may be determined for the decision-making, which describe the location of the data points in the two-dimensional entropy space. For example, the center of gravity of the data points may be calculated and the decision may be made based on the location of the center of gravity with respect to the threshold line. The said certain number of data points may vary according to the application involved. As mentioned above, the length of one epoch is typically of the order of a few seconds, in which case the final decision could be made based on 4 to 8 successive data points, for example.

In the above-described manner the mechanism of the invention thus indicates at each instant of time, which one of the EEG and EOG components is the currently dominating signal component. As mentioned above, this indication may be updated after each epoch or after a certain number of epochs.

The knowledge about the currently dominating signal component may then be utilized in various manners depending on the application in question. In one embodiment, for example, the spectral entropy of the currently dominant signal component may be used as a measure of the physiological condition of the subject. This additional step is shown as step 38 in FIG. 3. In this embodiment, both signal components have thus physiological significance. In practice, at one time instance the dominant component is identified and the spectral entropy of that component is used for monitoring. At the next time instance, the other component may be the dominant signal component, and its spectral entropy value is monitored.

However, if only one of the signal components, such as the EEG, has physiological significance, and the other signal component of interest, such as the EOG, is considered as an artifact, only the spectral entropy of the significant signal component is used for monitoring. However, the spectral entropy value of the significant component may be utilized only when the said component is identified as the dominant signal component. The spectral entropy values of the significant signal component, which were obtained during the latest dominance of the significant signal component, may be kept in a memory during the dominance of the insignificant signal component. If the dominance of the signal component considered as an artifact lasts too long in view of the application, the system may generate an indication that the quality of the signal is not sufficient.

Figure 5:
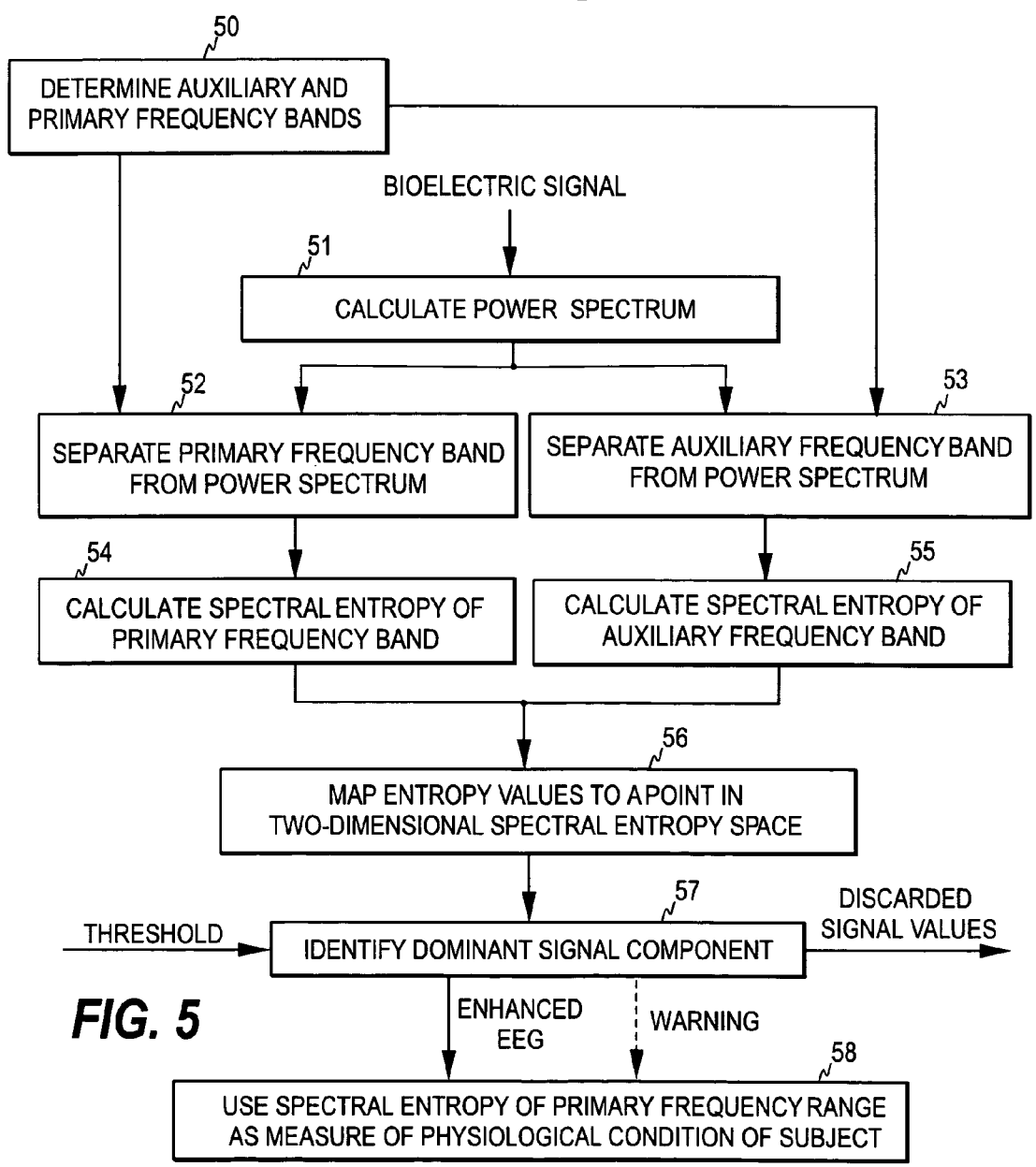
FIG. 5 is a flow diagram illustrating another embodiment of the invention, in which the decision-making is based on a two-dimensional indicator space.

FIG. 5 illustrates one embodiment, in which the EOG component is considered as an artifact. This embodiment corresponds to that of FIG. 3, except that a power spectrum is calculated at step 51 and the signal values are discarded when the EOG component is the dominant signal component. This is performed at step 57. Furthermore, at the last step 58, the spectral entropy of the primary frequency band only is used for the monitoring. The signal supplied from step 57 to the monitoring system is thus an enhanced EEG signal from which the artifact has been removed. If the dominance of the EOG signal lasts too long in view of the application, a warning indicating that the quality of the EEG signal is not high enough may be generated at step 57.

Figure 6:
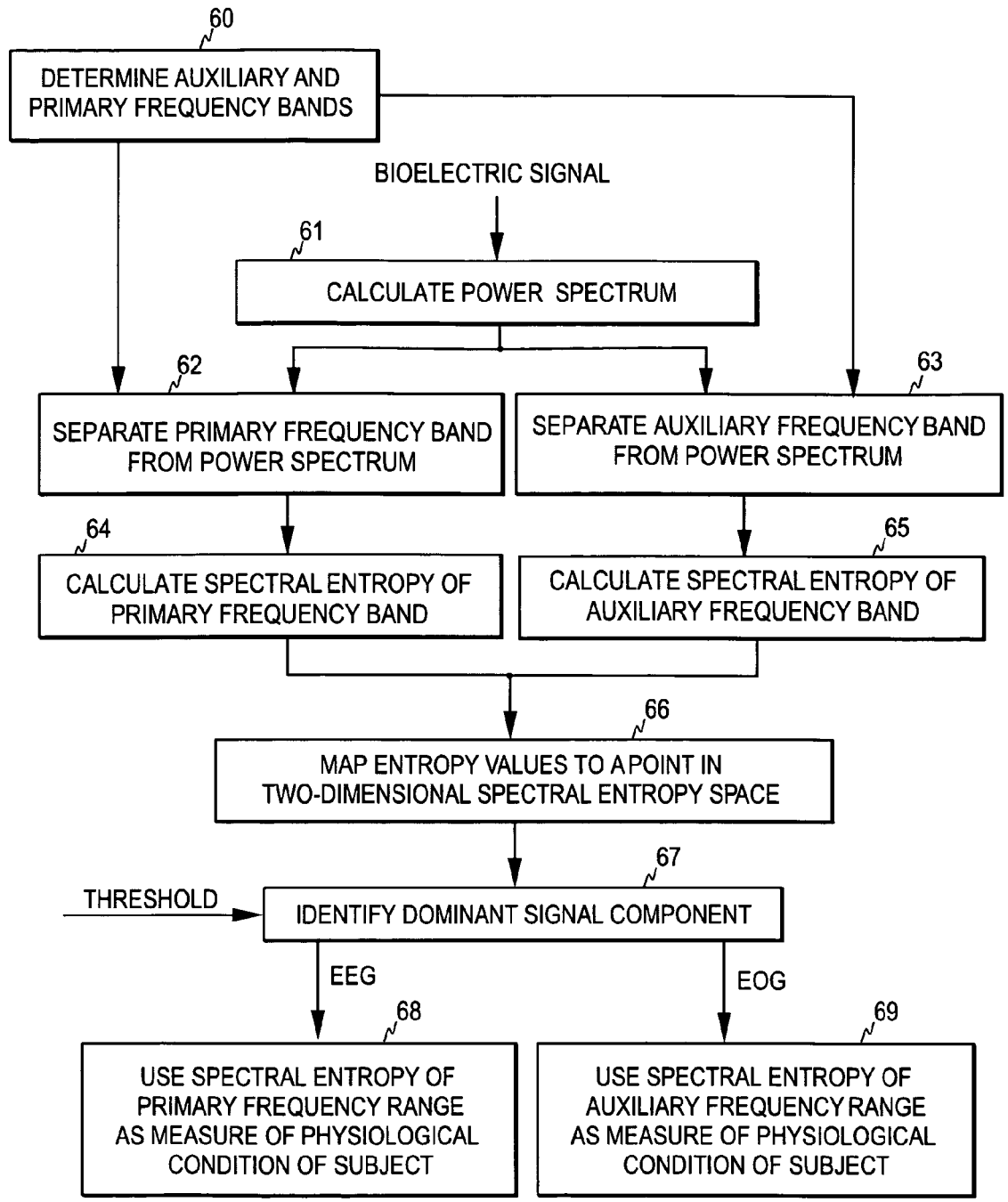
FIG. 6 is a flow diagram illustrating a further embodiment of the invention, in which the decision-making is also based on a two-dimensional indicator space.

FIG. 6 illustrates a further embodiment of the invention. This embodiment is similar to the previous embodiment, except that the EEG and the EOG signal components are monitored simultaneously at steps 68 and 69. This embodiment thus allows simultaneous monitoring of two different physiological systems of the subject, together with instantaneous tracking of the dominant signal component. When one signal component dominates, the spectral entropy value(s) measured during the latest dominance of the other signal component may be used for that signal component (provided that the dominance of the said one signal does not last too long in view of the application concerned).

Although equations (3) and (4) were applied to power spectrum above, they can also be applied to amplitude spectrum. However, the use of power spectrum is preferred, since it emphasizes the magnitude differences between frequency peaks. If the match between the original signal and a sine wave is exact, distinct peaks are observed in the obtained spectrum and the spectral entropy is low. When the match is poor, the obtained spectrum is flat and the spectral entropy is high. Due to its nature, the EOG has a poor match with a sine wave, whereas low frequency EEG has a good match.

As to the performance of the above method, one requirement is that the response time, i.e. the time required to detect the dominant component, is short enough. This is critical for example when the patient is anesthetized, as the transition from a conscious to an unconscious state occurs quickly. Since the above mechanism generally involves calculation of indicators indicative of spectral distribution, it is useful that a frequency resolution high enough is used for the DFT. The frequency resolution $\Delta f$ is inversely proportional to the signal length used in the Fourier transform:

$$\Delta f = \frac{f_s}{N}$$

where $f_s$ is the sampling frequency and N is the number of samples in the Fourier transform. For example, if 2000 samples, sampled at a rate of 400 Hz, are used in the Fourier transform, the frequency resolution obtained will be 0.2 Hz. Increasing the number of samples N enhances the frequency resolution. However, this makes the algorithm slower for indicating quick changes in the state of the subject. Therefore, in one embodiment of the invention zero padding may be used to achieve a good trade-off between the response time and the frequency resolution. In zero padding a series of zeros is added to the original signal samples. This series may be added either to the end or to the beginning of the original signal sequence at step 31, 51, and 61.

Instead of zero padding, or together with it, overlapping epochs may be used. In this embodiment, the time window is sliding in shorter steps than the window length. For example, steps of 2.5 seconds may be used with epochs of 5 seconds. In this way, more information is obtained. For example, 12 instead of 6 entropy value pairs are obtained in 30 seconds. This allows more rapid tracking of the subject state, since the time resolution is 2.5 seconds instead of 5 seconds.

Figure 7:
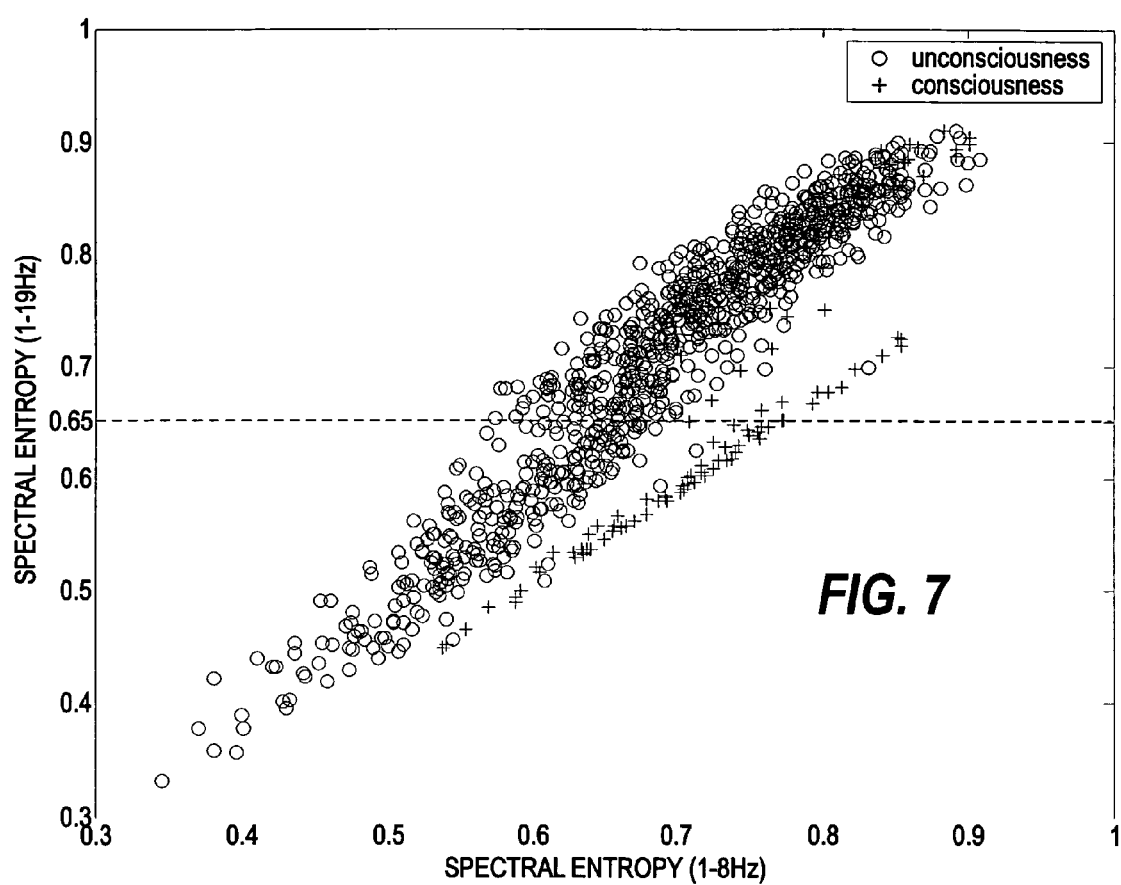
FIG. 7 is a scatterogram illustrating the mechanism of the invention.

FIG. 7 is a scatterogram showing the spectral entropies of the primary and auxiliary bands, the entropies being measured from a group of patients. In the figure, the circles represent entropy values obtained from unconscious patients, while the crosses represent entropy values obtained from conscious patients.

The eye movement causes the power of the signal spectrum to concentrate on the low frequencies. Therefore, low entropy values may be obtained even though the entropy calculated from a pure EEG signal would be high. The problem thus occurs at low spectral entropy values. If the spectral entropy of the primary frequency band is low, either EOG or low-frequency EEG activity may thus be present. However, if the spectral entropy of the primary frequency band is high, neither EOG nor low-frequency EEG activity is present. In FIG. 7, the threshold between the low and high entropy values is set to 0.65. When the existence of either EOG or low-frequency EEG is detected, the spectral entropies are examined in the above-described manner in the two-dimensional orthogonal entropy space defined by the primary and auxiliary frequency bands. As can be seen from the figure, low entropy values may be obtained on the primary band both from conscious and unconscious patients. In unconscious state, low entropy values result from the EEG activity, whereas in conscious state low entropy values result from the EOG component. As can be seen from FIG. 7, the data points involving an EOG component clearly deviate from the data points not including an EOG component. The EOG and low-frequency EEG can therefore be classified in the said two-dimensional space by using the above linear classification method.

In a further embodiment of the invention, the decision on the dominant signal component may be made based on mutual information and a single threshold value. In this embodiment, joint entropy of the primary and auxiliary frequency bands is calculated. Generally, joint entropy describes the amount of information necessary to specify the value of two discrete random variables. The joint entropy of a primary frequency band X and an auxiliary frequency band Y is:

$$S(X, Y) = \sum_{x \in X} \sum_{y \in Y} p(x, y) \log \frac{1}{p(x, y)},$$

where p(x,y) is the probability distribution of the predefined signal property, such as the frequency.

From the entropies of the primary and auxiliary frequency bands S(X) and S(Y), respectively, and from their joint entropy S(X,Y), the mutual information I(X;Y) may be derived as follows:

$$I(X;Y)=S(X)+S(Y)-S(X,Y)$$

Mutual information I(X;Y) describes the dependence of systems X and Y. When the mutual information is zero, systems are totally independent, and when the mutual information increases, systems become more dependent on each other.

Figure 8:
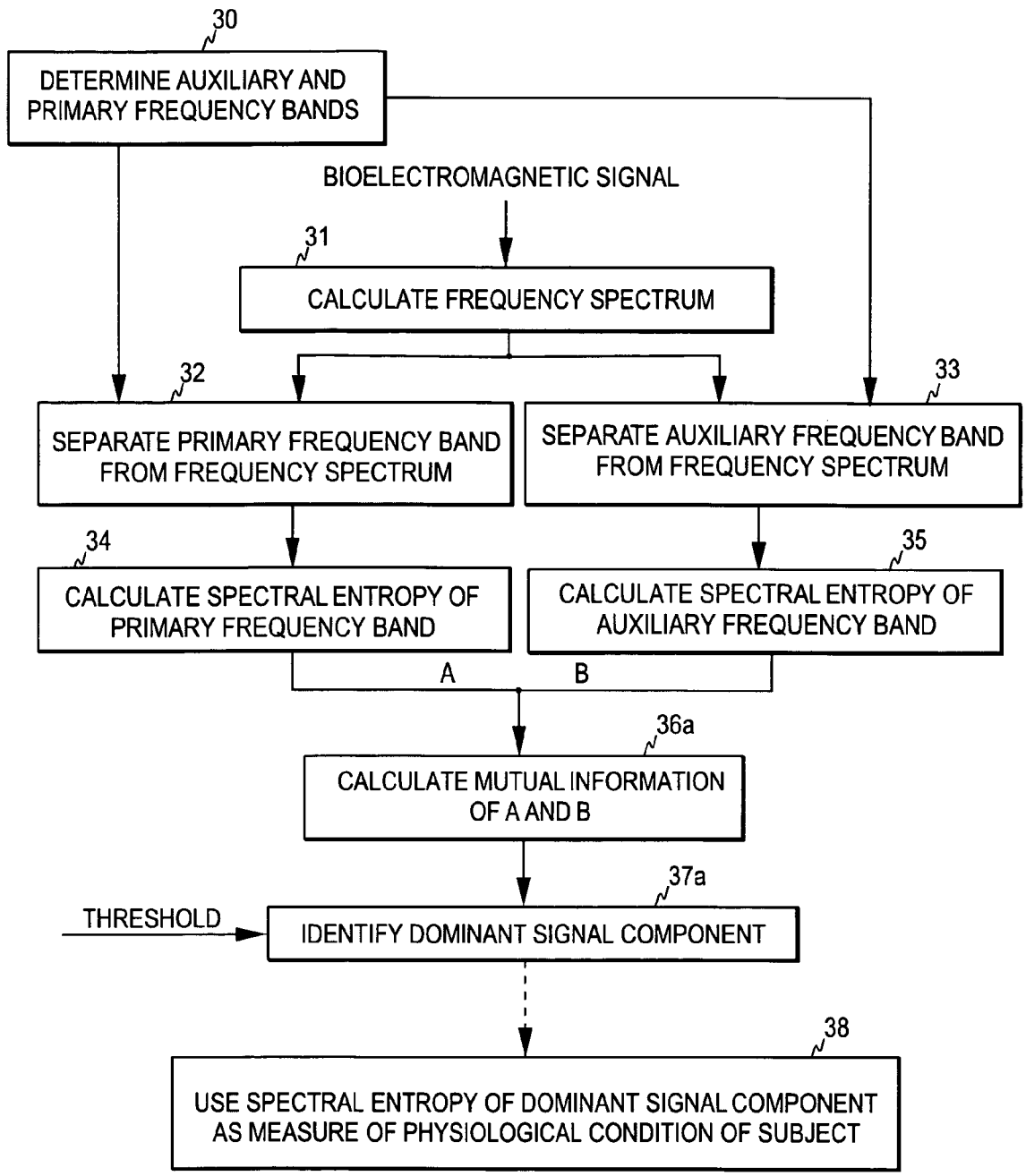
FIG. 8 is a flow diagram illustrating one embodiment of the invention; in which the decision-making is based on the mutual information of the spectral entropies.

FIG. 8 illustrates an example of the above-mentioned embodiment. Here, the embodiment corresponds to that of FIG. 3, except that the entropy value pair (A, B) is not mapped to a data point in the two-dimensional entropy space. Instead, the entropy value pair is supplied to step 36a, in which the mutual information of the value pair is calculated. As mentioned above, the mutual information I(A;B) may be calculated by first determining the joint entropy of the primary and auxiliary frequency bands and then subtracting the joint entropy from the sum of the entropies of the primary and auxiliary frequency bands. The mutual information, which is obtained for each epoch, is then compared with a predefined threshold value at step 37a in order to identify the dominant component. In this embodiment, the threshold is thus a single value. The final decision on the dominant signal component may be made after each epoch or after a sequence of epochs, as discussed above.

Figure 9:
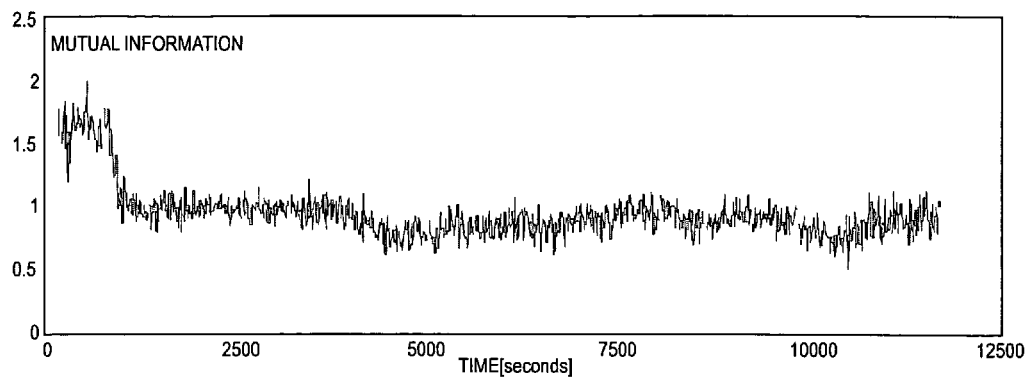
FIG. 9 illustrates the use of the mutual information as an indicator of the dominant signal component.

FIG. 9 shows an example of the mutual information determined based on the signal data of FIG. 1. As can be seen from the figure, there is a clear change in the mutual information when the EOG component disappears from the composite signal, which takes place around t=900 seconds, cf. FIG. 1. The mutual information is thus a good indicator of the dominant signal component.

Figure 10:
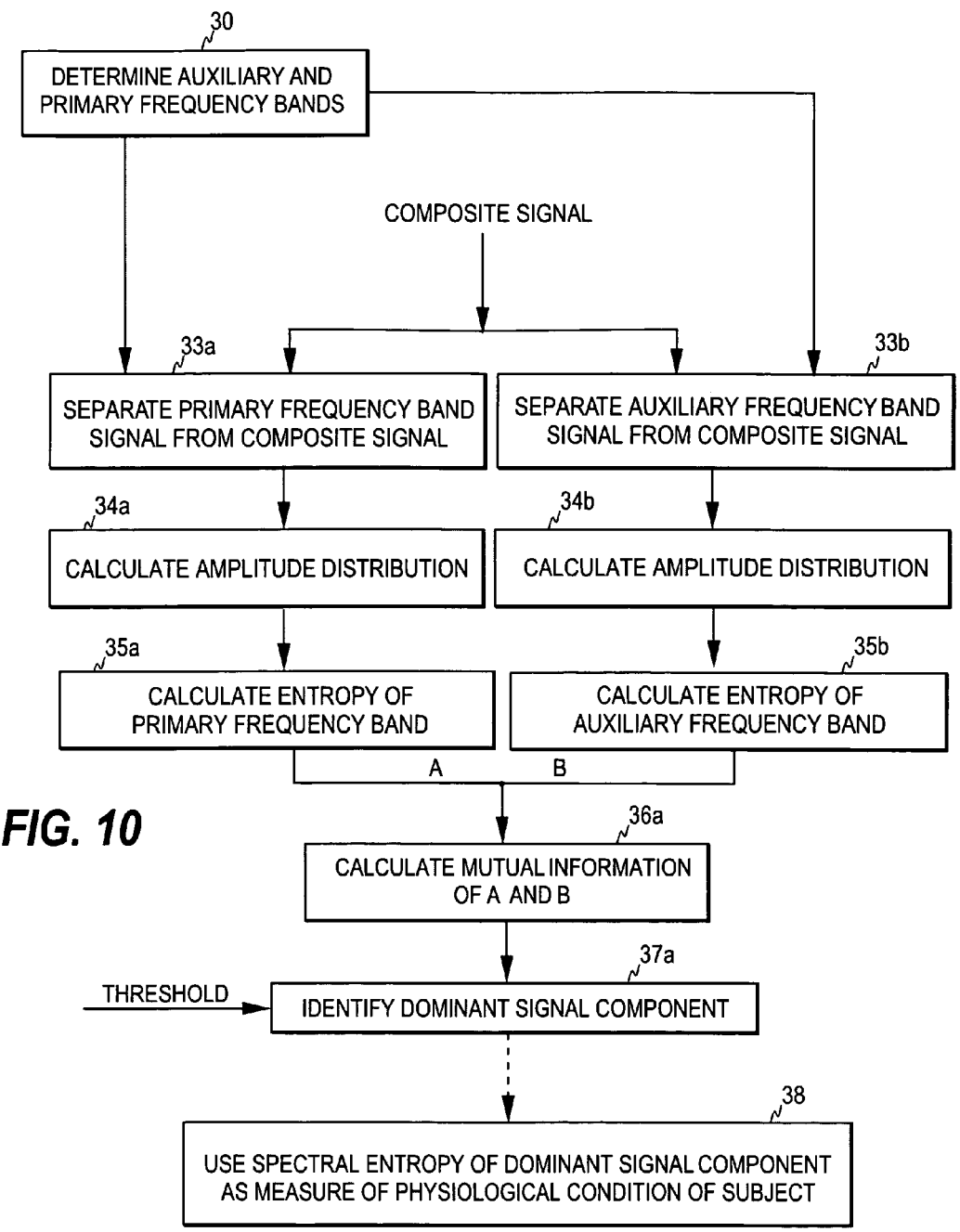
FIG. 10 is a flow diagram illustrating a still further embodiment of the invention, in which the decision-making is based on the mutual information calculated based on amplitude distributions.

Above, the mutual information was derived from the spectral entropies of the primary and auxiliary frequency bands. However, it may also be derived from the entropies of amplitude distributions (probability mass function) of the composite signal. FIG. 10 illustrates how the method changes as compared to the embodiment of FIG. 8 when amplitude distributions are utilized instead of spectral distributions. In this case, the frequency spectrum is not calculated but the composite signal is first filtered at steps 33a and 33b to obtain the signal data corresponding to the primary and auxiliary frequency bands, respectively. The amplitude distribution on the primary frequency band is then calculated at step 34a and the amplitude distribution on the auxiliary frequency band at step 34b. Next, the entropy of the primary frequency band is calculated at step 35a, and the entropy of the auxiliary frequency band at step 35b, whereby an entropy value pair (A; B) is obtained (for each epoch). The remaining steps are as described in connection with the embodiment of FIG. 8.

The primary and auxiliary bands may also be selected so that the second signal component is regarded as an undesired signal component when determining the primary frequency band, and the first signal component is regarded as an undesired signal component when determining the auxiliary frequency band. In this way, the primary and auxiliary frequency bands become non-overlapping. This possibility applies especially to the embodiments utilizing the mutual information.

Figure 2:
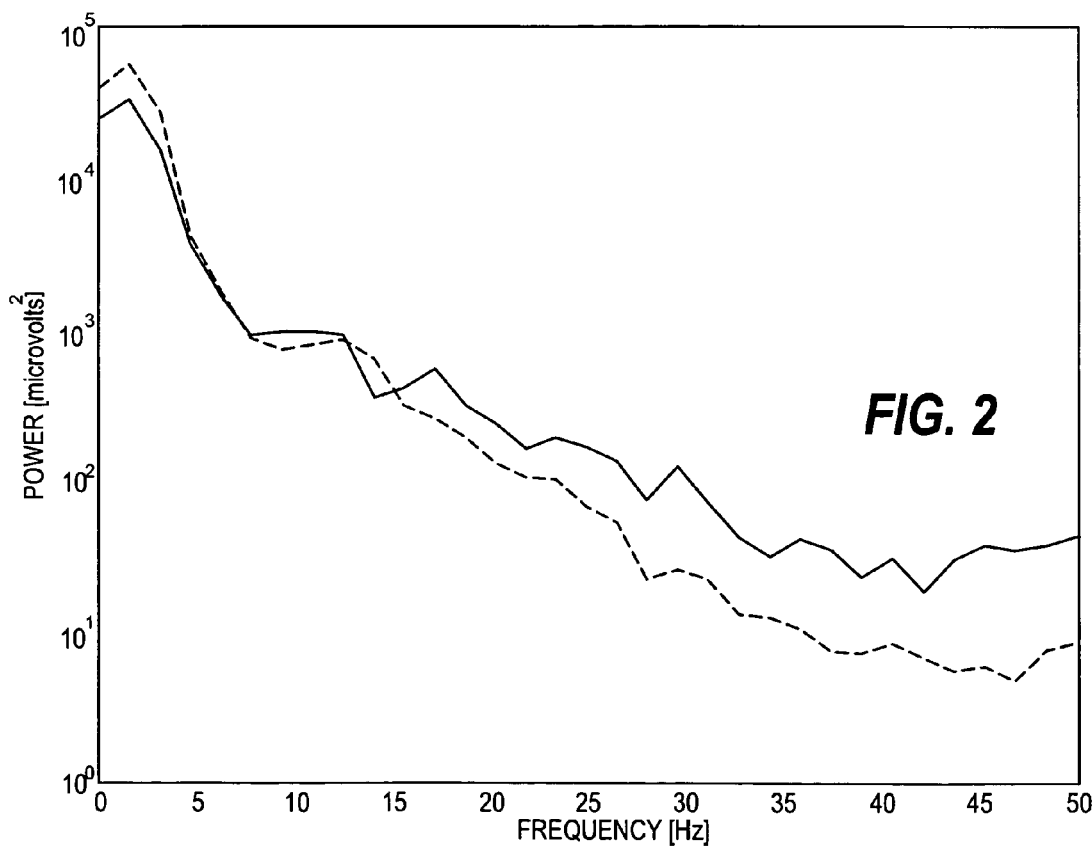
FIG. 2 illustrates the problem behind the invention by showing a spectrum of a pure EEG signal and a spectrum of an EEG signal comprising EOG and EMG components.
Figure 11:
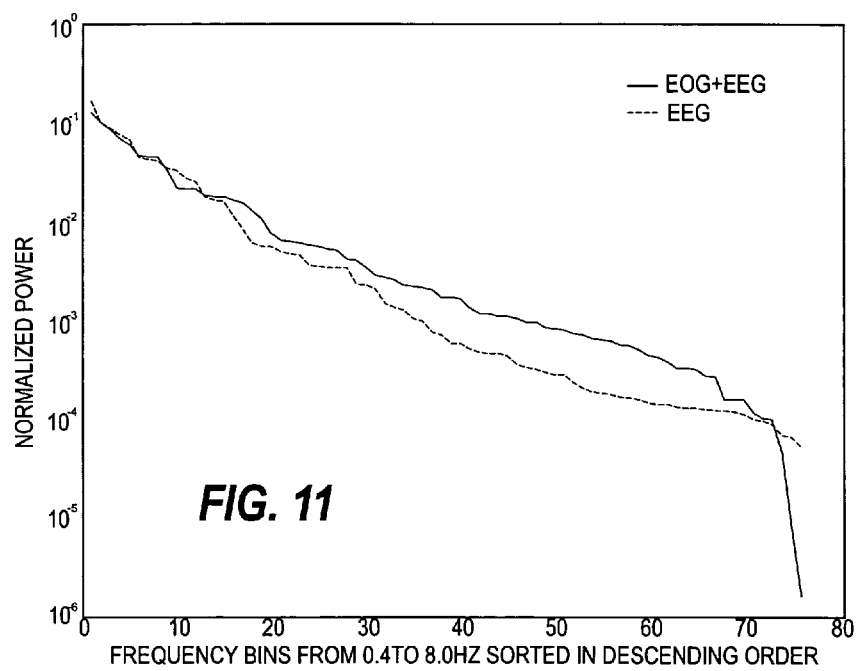
FIG. 11 illustrates the identification mechanism of the invention.

FIG. 11 illustrates how the method of the invention detects the dominant signal component. In FIG. 11, the same signal data has been used as in connection with FIG. 2. Each curve in FIG. 11 has been obtained by first calculating the power spectrum of the respective signal with an improved frequency resolution (as compared to FIG. 2). The values of the power spectrum on a frequency band of 0.4 to 8 Hz have then been normalized so that their total value is one, and the obtained values have been sorted in descending order. As can be seen from the figure, the curve attenuates slower when the EOG component is present in the signal. The presence of the EOG component thus widens the spectral distribution on the band in question, i.e. the power is less heavily distributed to certain distinct frequencies when the EOG component is present in the signal. As discussed above, this difference may be seen in the spectral entropy. However, any indicator that similarly reveals the differences in the spectral distributions may be used.

Figure 12:
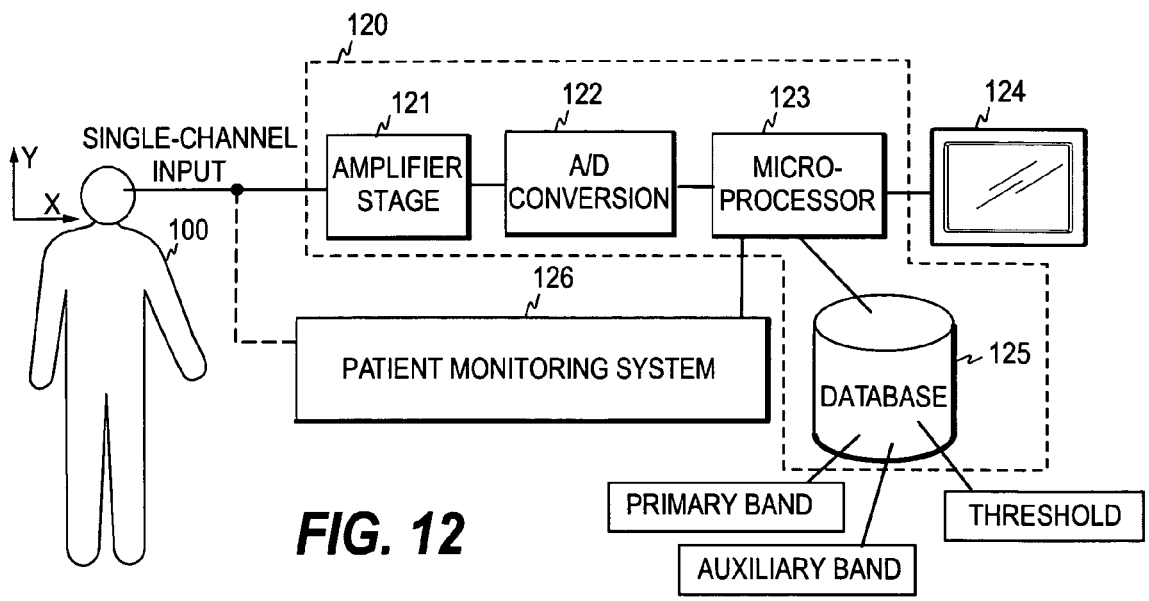
FIG. 12 illustrates one embodiment of the system according to the invention.

FIG. 12 illustrates one embodiment of the system according to the invention. The single-channel input data is obtained from a sensor attached to a patient 100. The signal is first supplied to an amplifier stage 121, which amplifies the signal before it is sampled and converted into digitized format in an A/D converter 122. The digitized signal is supplied to a microprocessor 123 which is provided with a database or memory unit 125 holding the digitized signal data obtained from the sensor. The database may further hold the parameters needed for the above-described operation, such as the limits of the primary and auxiliary frequency bands and the data defining the threshold line.

The microprocessor calculates an entropy value pair for each epoch, compares the value pair to the threshold, and makes a decision on the dominant signal component using one of the above decision-making methods. It may also display the results on the screen of a monitor 124 connected to the microprocessor. As discussed above, the monitoring system may utilize only one of the components of interest, the component being the currently dominating component, or both components of interest. Depending on the case, the microprocessor supplies the relevant spectral entropy values to the actual monitoring system 126.

The software enabling a conventional measurement device 120, such as an EEG measurement device, to detect the dominant signal component may also be delivered separately to the measurement device, for example on a data carrier, such as a CD or a memory card. In other words, a conventional measurement device may be upgraded by a plug-in unit that includes software enabling the measurement device to identify the dominant signal component based on the signal data it has obtained from the subject.

In order to achieve optimal detection of the EOG signal component, it is preferable to attach the electrodes diagonally so that one of the electrodes is close to the eyes, for example between the eyebrows of the patient. Diagonal here refers an electrode arrangement in which the measuring electrodes are placed at different levels both in the x direction and in the y direction shown in FIG. 12. This kind of measuring arrangement is shown in U.S. Patent Application 20040204656.

Although the invention was described above with reference to the examples shown in the appended drawings, it is obvious that the invention is not limited to these, but may be modified by those skilled in the art without departing from the scope and spirit of the invention. For example, the mechanism may be used for identifying any signal components of interest, whose proportions in the biosignal may be detected by the above mechanism.

The invention claimed is:

1. A method for identifying a dominant signal component in a biosignal obtained from a subject, the method comprising the steps of:
   obtaining a biosignal from a subject, the biosignal including a first signal component having a first frequency range and a second signal component having a second frequency range;
   determining a first indicator in a microprocessor, the first indicator characterizing the probability distribution of a predefined property of the biosignal on a primary frequency band including at least part of the first frequency range;
   determining a second indicator in the microprocessor, the second indicator characterizing the probability distribution of said predefined property of the biosignal on an auxiliary frequency band including at least part of the second frequency range; and
   identifying, in the microprocessor, based on the first and second indicators, which one of the first and second signal components is currently a dominant signal component in the biosignal.

2. A method according to claim 1, further comprising the steps of:
   defining a first frequency band and a second frequency band, which maximally cover, respectively, the first and second frequency ranges and which are at the same time minimally disturbed by any undesired signal component within the biosignal; and
   selecting the primary and auxiliary frequency bands, respectively, based on the first and second frequency bands.

3. A method according to claim 2, wherein the selecting step includes selecting the first frequency band as the primary frequency band and the second frequency band as the auxiliary band.

4. A method according to claim 1, wherein the determining steps include determining the first and second indicators, and wherein the first and second indicators characterize the probability distribution of the frequency of the biosignal on the primary and auxiliary frequency bands, respectively.

5. A method according to claim 4, wherein the first and second indicators are indicative of spectral entropy of the biosignal on the primary and auxiliary frequency bands, respectively.

6. A method according to claim 4, wherein the identifying step includes a sub-step of defining a data point in a two-dimensional indicator space defined by the first and second indicators, the data point being determined by current values of the first and second indicators.

7. A method according to claim 6, wherein the identifying step includes the sub-steps of:
   comparing the location of the data point in the two-dimensional indicator space with a predetermined threshold; and
   deciding on the dominant signal component based on the comparing step.

8. A method according to claim 4, wherein the identifying step includes a sub-step of defining the mutual information of the first and second indicators.

9. A method according to claim 8, wherein the identifying step further includes the sub-steps of:
   comparing the mutual information with a predefined threshold value; and
   making a decision on the dominant signal component based on the comparing step.

10. A method according to claim 1, wherein the determining steps include determining the first and second indicators, and wherein the first and second indicators characterize the probability distribution of the amplitude of the biosignal on the primary and auxiliary frequency bands, respectively.

11. A method according to claim 10, wherein the identifying step includes a sub-step of defining the mutual information of the first and second indicators.

12. A method according to claim 11, wherein the identifying step further includes the sub-steps of:
   comparing the mutual information with a predefined threshold value; and
   making a decision on the dominant signal component based on the comparing step.

13. A method according to claim 1, wherein the determining steps include determining a sequence of indicator pairs, each indicator pair including the first and second indicators obtained during a certain measurement period.

14. A method according to claim 13, wherein the identifying step includes a sub-step of defining a sequence of data points in a two-dimensional indicator space defined by the first and second indicators, each data point being determined by the corresponding indicator pair.

15. A method according to claim 14, wherein the identifying step further includes a sub-step of calculating a measure indicative of the location of the sequence of data points in the two-dimensional indicator space.

16. A method according to claim 15, wherein the identifying step further includes a step of comparing the measure with a predetermined threshold.

17. A method according to claim 14, wherein the identifying step further includes the sub-steps of:
   comparing a selected one of the data points with a predetermined threshold;
   selecting one of the first and second signal components as a dominant signal component based on the comparing sub-step, the comparing and selecting sub-steps being performed for each data point in the sequence of data points, whereby the dominant signal component is selected a plurality of times; and
   making a final decision on the dominant signal component based on the selecting sub-step.

18. A method according to claim 13, wherein the sub-step of making the final decision includes defining which one of the first and second signal components is selected as the dominant signal component most often.

19. A method according to claim 13, further comprising the steps of:
   defining a mutual information value for each indicator pair in the sequence, whereby a sequence of mutual information values is obtained; and
   selecting the dominant signal component based on the sequence of mutual information values.

20. A method according to claim 1, further comprising a step of monitoring a selected indicator of the first and second indicators, the selected indicator being the first indicator when the first signal component is the dominant signal component and the second indicator when the second signal component is the dominant signal component.

21. A method according to claim 1, further comprising a step of monitoring both the first and second indicators.

22. A method according to claim 21, wherein the monitoring step includes using previous values of the second indicator when the first signal component is the dominant signal component and previous values of the first indicator when the second signal component is the dominant signal component.

23. A method according to claim 1, further comprising a step of monitoring a selected indicator of the first and second indicators, the monitoring step being performed when the one of the first and signal components that corresponds to the selected indicator is the dominant signal component.

24. A method according to claim 23, further comprising a step of regarding the biosignal as a corrupted signal when the one of the first and signal components that corresponds to the selected indicator fails to be the dominant signal component.

25. A system for identifying a dominant signal component in a biosignal obtained from a subject, the system comprising:
measurement means for obtaining a biosignal from a subject, the biosignal including a first signal component having a first frequency range and a second signal component having a second frequency range;
first calculation means for determining a first indicator characterizing the probability distribution of a predefined property of the biosignal on a primary frequency band including at least part of the first frequency range;
second calculation means for determining a second indicator indicative of the probability distribution of the predefined property of the biosignal on an auxiliary frequency band including at least part of the of the second frequency range; and
identification means for identifying, which one of the first and second signal components is currently a dominant signal component in the biosignal, the identification means being responsive to the first and second calculation means.

26. A system according to claim 25, wherein the first and second indicators characterize the probability distribution of the frequency of the biosignal on the primary and auxiliary frequency bands, respectively.

27. A system according to claim 26, wherein the first and second indicators are indicative of spectral entropy of the biosignal on the primary and auxiliary frequency bands, respectively.

28. A system according to claim 26, wherein the identification means are configured to define a data point in a two-dimensional indicator space defined by the first and second indicators, the data point being determined by current values of the first and second indicators.

29. A system according to claim 28, wherein the identification means are configured to compare the location of the data point in the two-dimensional indicator space with a predetermined threshold and to decide on the dominant signal component based on the comparison.

30. A system according to claim 25, wherein the first and second indicators characterize the probability distribution of the amplitude of the biosignal on the primary and auxiliary frequency bands, respectively.

31. A system according to claim 25, wherein the primary frequency band represents a frequency band which maximally covers the first frequency range and which is at the same time minimally disturbed by any undesired signal components within the biosignal, and the auxiliary frequency band represents a frequency band which maximally covers the second frequency range and which is at the same time minimally disturbed by any undesired signal components within the biosignal.

32. A system according to claim 25, wherein the first and second calculation means are configured to calculate a sequence of indicator pairs, each indicator pair including the first and second indicators obtained during a certain measurement period.

33. A system according to claim 32, wherein the identification means are further configured to define a sequence of data points in a two-dimensional indicator space defined by the first and second indicators, each data point being determined by the corresponding indicator pair.

34. A system according to claim 33, wherein the identification means are further configured to calculate a measure indicative of the location of the sequence of data points in the two-dimensional indicator space.

35. A system according to claim 34, wherein the identification means are further configured to compare the measure with a predetermined threshold.

36. A system according to claim 25, wherein the identification means are configured to define the mutual information of the first and second indicators.

37. A system according to claim 36, wherein the identification means are further configured to compare the mutual information with a predefined threshold value.

38. A system according to claim 36, wherein the identification means are further configured to define a mutual information value for each indicator pair in the sequence of indicator pairs, whereby a sequence of mutual information values is obtained, and to select the dominant signal component based on the sequence of mutual information values.

39. A system for identifying a dominant signal component in a biosignal obtained from a subject, the system comprising:
measurement device configured to measure a biosignal from a subject, the biosignal including a first signal component having a first frequency range and a second signal component having a second frequency range;
a first calculator, responsive to the measurement device, configured to determine a first indicator characterizing the probability distribution of a predefined property of the biosignal on a primary frequency band including at least part of the first frequency range;
a second calculator, responsive to the measurement device, configured to determine a second indicator characterizing the probability distribution of the predefined property of the biosignal on an auxiliary frequency band including at least part of the second frequency band; and
identification means for identifying, which one of the first and second signal components is currently a dominant signal component in the biosignal, the identification means being responsive to the first and second calculators.

40. A system according to claim 39, wherein the first and second indicators characterize the probability distribution of the frequency of the biosignal on the primary and auxiliary frequency bands, respectively.

41. A system according to claim 40, wherein the first and second indicators are indicative of spectral entropy of the biosignal on the primary and auxiliary frequency bands, respectively.

42. A system according to claim 39, wherein the first and second indicators characterize the probability distribution of the amplitude of the biosignal on the primary and auxiliary frequency bands, respectively.

43. A computer program product stored on a computer readable medium for identifying a dominant signal component in a biosignal obtained from a subject, the computer program product comprising:
a first program code portion stored on a computer readable medium configured to determine a first indicator characterizing the probability distribution of a predefined property of the biosignal on a selected primary frequency band;

a second program code portion stored on a computer readable medium configured to determine a second indicator characterizing the probability distribution of the predefined property of the biosignal on a selected auxiliary frequency band; and a third program code portion stored in a computer readable medium configured to identify, based on the first and second indicators, which one of the first and second signal components is currently a dominant signal component in the biosignal.

44. A computer program product according to claim 43, wherein the first and second program code portions are configured to determine the first and second indicators, respectively, in which the first and second indicators characterize the probability distribution of the frequency of the biosignal on the primary and auxiliary frequency bands, respectively.

45. A computer program product according to claim 43, wherein the first and second program code portions are configured to determine the first and second indicators, respectively, in which the first and second indicators characterize the probability distribution of the amplitude of the biosignal on the primary and auxiliary frequency bands, respectively.

* * * * *

UNITED STATES PATENT AND TRADEMARK OFFICE
CERTIFICATE OF CORRECTION

PATENT NO. : 7,625,340 B2
APPLICATION NO. : 11/002402
DATED : December 1, 2009
INVENTOR(S) : Mika Särkelä

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1398 days.

Signed and Sealed this

Twenty-sixth Day of October, 2010

David J. Kappos
*Director of the United States Patent and Trademark Office*